United States Patent [19]

Rothrum

[11] Patent Number: 5,832,925
[45] Date of Patent: Nov. 10, 1998

[54] SURGICAL DRAPE HAVING IMPROVED SEALING APPARATUS

[75] Inventor: Robert J. Rothrum, Coon Rapids, Minn.

[73] Assignee: Minnesota Mining and Manufacturing Company, St. Paul, Minn.

[21] Appl. No.: 871,172

[22] Filed: Jun. 9, 1997

[51] Int. Cl.$^6$ .................................................. A61B 19/00
[52] U.S. Cl. ...................................... 128/849; 128/853
[58] Field of Search ................................ 128/849–856

[56] References Cited

U.S. PATENT DOCUMENTS

| | | | |
|---|---|---|---|
| 4,974,604 | 12/1990 | Morris | 128/853 |
| 5,143,091 | 9/1992 | Patnode et al. | 128/853 |
| 5,158,553 | 10/1992 | Berry et al. | 604/248 |
| 5,192,301 | 3/1993 | Kamiya et al. | 606/213 |
| 5,345,946 | 9/1994 | Butterworth | 128/853 |
| 5,366,478 | 11/1994 | Brinkerhoff et al. | 660/213 |
| 5,419,343 | 5/1995 | Taylor | 128/853 |
| 5,494,050 | 2/1996 | Reyes | 128/853 |

FOREIGN PATENT DOCUMENTS

WO 95/24864  9/1995  WIPO .

OTHER PUBLICATIONS

Information on glove box from Plastic Scientific Lab, "The Fisher Catalog", ©1990 Fisher Scientific Brochure on Series H Iris Diaphragm Valves from MUCON Products.
Brochure on polymer glove boxes, Terra Universal, Inc.
Misc. information on glove boxes.
Brochure for 3M 1194 Steri–Drape Limb Sheet with Fluid Collection, 3M Health Care, 1994.

*Primary Examiner*—Michael A. Brown
*Attorney, Agent, or Firm*—F. Andrew Ubel

[57] ABSTRACT

An apparatus for sealing an environment defined by a periphery is provided. The sealing apparatus includes a first frame defining an opening and being disposed on the periphery of the environment and a second frame defining an opening. A flexible material is rotatably interconnected between the first frame opening and the second frame opening to form an iris aperture. The size of the iris aperture can be adjusted by rotating the second frame with respect to the first frame. The first frame may be secured with respect to the second frame in order to fix the size of the iris aperture. For securing the frames with respect to one another, hook and loop fastening material may be provided. The environment and periphery may, for example, be a surgical patient and a surgical drape, respectively.

20 Claims, 5 Drawing Sheets

5,832,925

1

SURGICAL DRAPE HAVING IMPROVED SEALING APPARATUS

FIELD OF THE INVENTION

The present invention is directed generally to a sealing apparatus and, more particularly, to a surgical drape having an improved sealing apparatus.

BACKGROUND OF THE INVENTION

Sealing apertures are used in a variety of industries to seal one environment from another. For example, in orthopedic surgery, a surgical drape having a sealing aperture is typically used to seal a patient from the limb on which an operation is performed. One commonly used orthopedic surgery drape includes an elastic aperture which receives the patient's limb. This type of orthopedic surgery drape generally includes an elastic sheet disposed between two outer sheets of material, one of the sheets typically being fluid resistant and the other fluid absorbent. The elastic sheet includes a self-sealing aperture which is disposed within openings formed in the outer sheets of material.

In use, these ortho-surgical drapes with self-sealing elastic apertures are prone to problems. The unstretched size of the self-sealing aperture is typically small enough to form a seal around the smallest sized limb which will be inserted therethrough. Patients having larger limbs often suffer from excessive and uncomfortable skin tension due to the relatively small self-sealing elastic film aperture. Fabrication of ortho-surgical drapes having self-sealing apertures is also problematic. Typically, such fabrication involves an expensive multiple-step process in which the elastic material (defining the self-sealing aperture) is heat-sealed or sonic-sealed between the outer sheets of material.

What is needed is an improved and less expensive surgical drape having a sealing aperture. The present invention addresses these as well as other needs.

SUMMARY OF THE INVENTION

The present invention generally relates to a sealing apparatus for sealing one environment from another environment. In accordance with one embodiment of the invention, an apparatus for sealing or isolating an environment defined by a periphery is provided. The sealing apparatus includes a first frame defining an opening and being disposed on the periphery of the environment and a second frame defining an opening. A flexible material is rotatably interconnected between the first frame opening and the second frame opening to form an iris aperture. The size of the iris aperture can be adjusted by rotating the second frame with respect to the first frame. The first frame may be secured with respect to the second frame in order to fix the size of the iris aperture. For securing the frames with respect to one another, a suitable fastening material (such as, e.g., a hook and loop material) may be provided.

In accordance with another embodiment of the invention, a surgical drape is provided. The surgical drape includes a drape sheet having a first frame defining an opening capable of receiving a limb, a second frame defining an opening capable of receiving the limb, and a flexible material rotatably interconnected between the first frame opening and the second frame opening and forming an iris aperture capable of receiving the limb. The size of the iris aperture can be adjusted by rotating the second frame with respect to the first frame.

The above summary of the present invention is not intended to describe each illustrated embodiment or every

2 implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
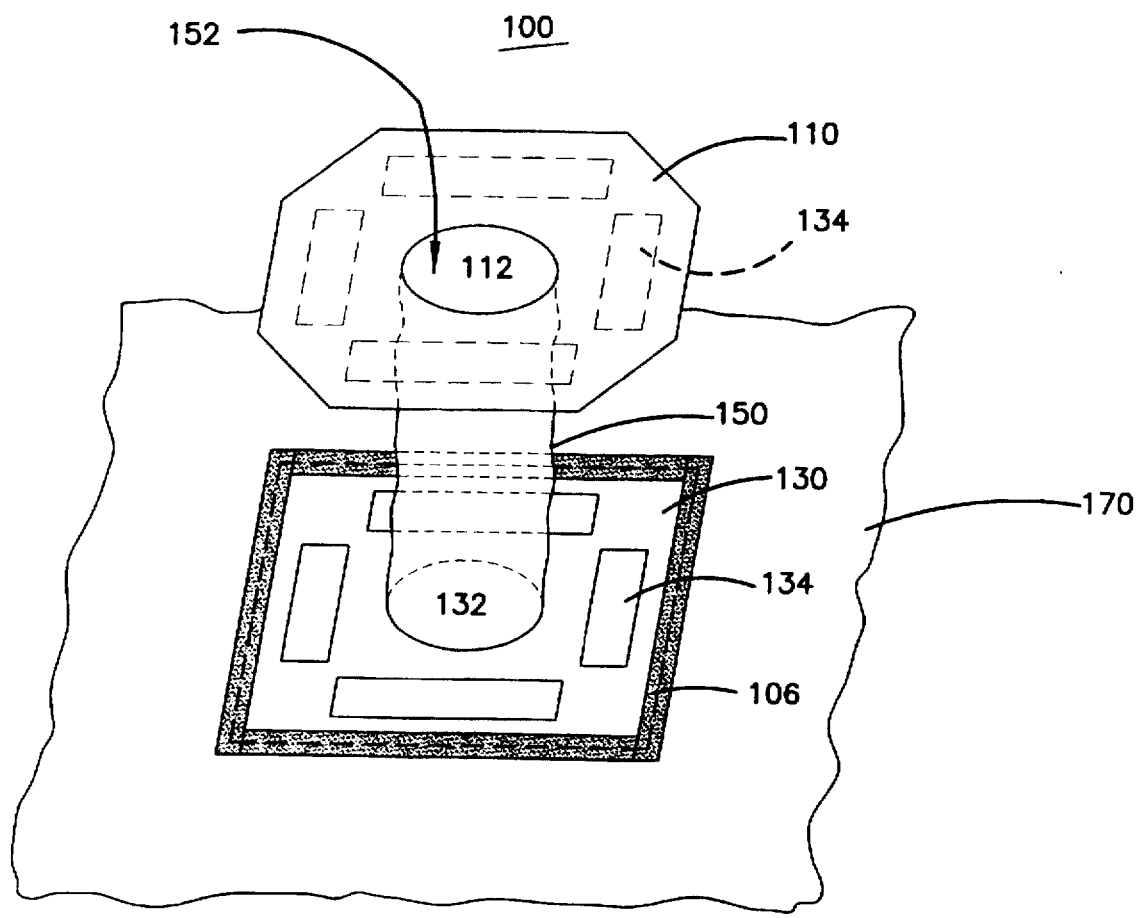
FIG. 1 illustrates an exemplary sealing apparatus in accordance with one embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

The present invention is believed to be applicable to a number of applications employing a sealing apparatus, including in particular surgical drapes. While the present invention is not so limited, an appreciation of various aspects of the invention will be gained through a discussion of the examples provided below.

The present invention generally provides a sealing apparatus for sealing one environment (the sealed environment) from another. The sealed environment is generally defined by a periphery and can vary widely depending on the application. For example, the environment may be a surgical patient with the periphery of the environment being defined by a surgical drape, or the environment may be the volume of a container with the periphery of the environment being defined by the container itself. The sealing apparatus generally includes two frames (preferably plates, more preferably thin plates) each having an opening and a flexible material rotatably interconnected between the frame openings. One of the frames is typically attached to or integrally formed from the periphery of the sealed environment. The flexible material generally forms an iris aperture which may be sealed by rotating the frames with respect to one another.

Figure 2:
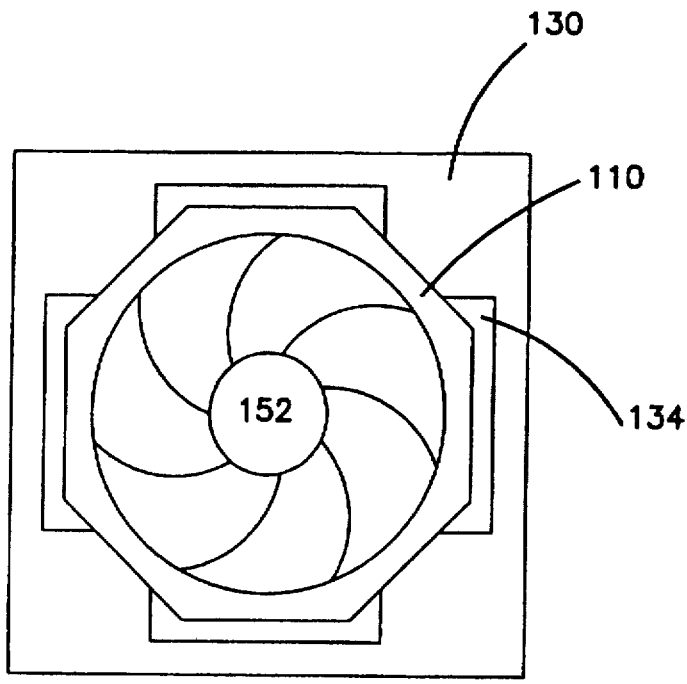
FIG. 2 illustrates the exemplary sealing apparatus shown in FIG. 1 with an open iris aperture.
Figure 3:
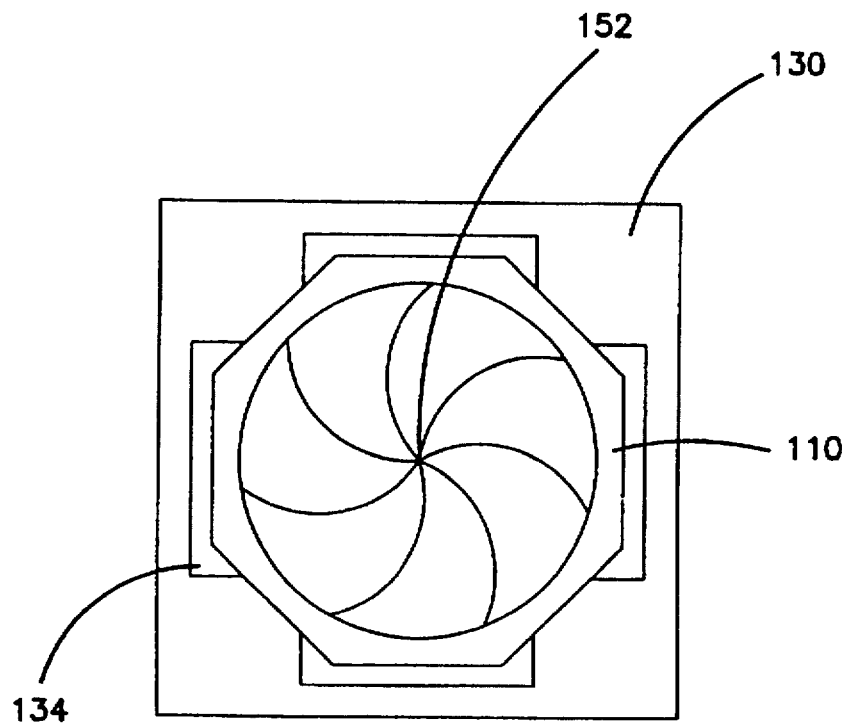
FIG. 3 illustrates the exemplary sealing apparatus shown in FIG. 1 with a closed iris aperture.

Turning now to FIG. 1, there is illustrated an exemplary sealing apparatus 100 for sealing off an environment defined by a periphery 170 in accordance with one embodiment of the present invention. The sealing apparatus 100 generally includes two frames 110 and 130 having openings 112 and 132 respectively, and a flexible material 150 rotatably interconnecting the two frames 110 and 130. The flexible material 150 generally forms an iris aperture 152 having a size which can be adjusted by rotating the two frames 110 and 130 with respect to one another. This, for example, allows the iris aperture 152 to be opened and closed, as illustrated in FIGS. 2 and 3, respectively. This also allows the iris aperture 152 to be sealingly closed about an object disposed in the iris aperture 152. Suitable flexible material includes, for example, tubular plastic material having a circular cross-section. Suitable material for the frames 110 and 130 includes, for example, plastic material, cardboard, etc.

The two frames 110 and 130 may be secured with respect to one another in a wide variety of manners in order to fix the size of the iris aperture 152. In the exemplary embodiment, for example, both frames 110 and 130 include fastening structure 134 which is used to secure the frames together. The fastening structure may be provided on the sides of the frames which face one another. In alternate embodiments, only one of the frames 110 or 130 may include fastening structure as will be discussed below. In one embodiment the frame 110 includes fastening structure 134 of hook material and the frame 130 includes fastening structure 134 of loop material such that, when the two frames are pressed together, the hook material and loop material interconnect to secure the frames together. Suitable hook and loop fastening systems include, for example, 3M's Microhook System®. 3M's Microhook System® is particularly advantageous as it provides a slim profile (preferably having a combined thickness of less than about 2 mm, more preferably less than about 1 mm) and thus a tighter seal at the iris aperture 152. However, it should be appreciated that other hook and loop fastening systems may be used.

In other embodiments, the frames 110 and 130 may be secured together in other manners. For example, each of the frames 110 and 130 may include magnetic fastening material 134, such as magnetic tape, having opposing polarities for securing the frames together. Suitable magnetic tape includes adhesive-coated magnetic film, for example. In other embodiments, one or both of the frames 110 and 130 may include an adhesive fastening material 134, such as adhesive tape, for securing the frames together. For example, a non-tacky adhesive tape (such as is disclosed in U.S. patent application Ser. No. 08/709,241, which is herein incorporated by reference) or a repositionable adhesive tape may be provided on one of the frames 110 or 130 for attaching the frames together. Suitable tapes include, for example, 3MJ2000 tape or 3M refastenable tape or 3M Very High Bond tape. In yet another embodiment, one or both of the frames 110 and 130 may include a permanent adhesive fastening material 134, such as a double-sided adhesive tape, to permanently secure the frames together. This embodiment would be particularly advantageous in a single use application.

To facilitate grasping, rotating, and/or securing frame 110 to frame 130, one or both frames may have a noncircular shape, such as a octagonal shape. However it should be appreciated that the invention is not limited to noncircular frames as other frame shapes such as circular shapes or ring shapes may be used with the present invention.

The frame assembly 100 is generally attached to the environment periphery 170 such that an opening in the periphery 170 is substantially aligned with the opening 132 of the frame 130 so as to form a passageway through the sealing apparatus to the sealed environment. The size of the periphery opening and the frame openings 112 and 132 are suitably selected in consideration of the desired application of the sealing apparatus 100.

The sealing apparatus 100 may be attached to the periphery 170 by attaching frame 130 to the periphery 170 using a fastener such as tape 106. The tape 106 may, for example, be disposed about the perimeter of the frame 130 and seal the sealing apparatus to the periphery 170. The invention is not limited to tape, however. Other types of fasteners may be used to attach the sealing apparatus 100 to the periphery 170. In other embodiments, as will be discussed further below, one frame of a sealing apparatus may be integrally formed from a portion of the periphery of a sealed environment.

Figure 4:
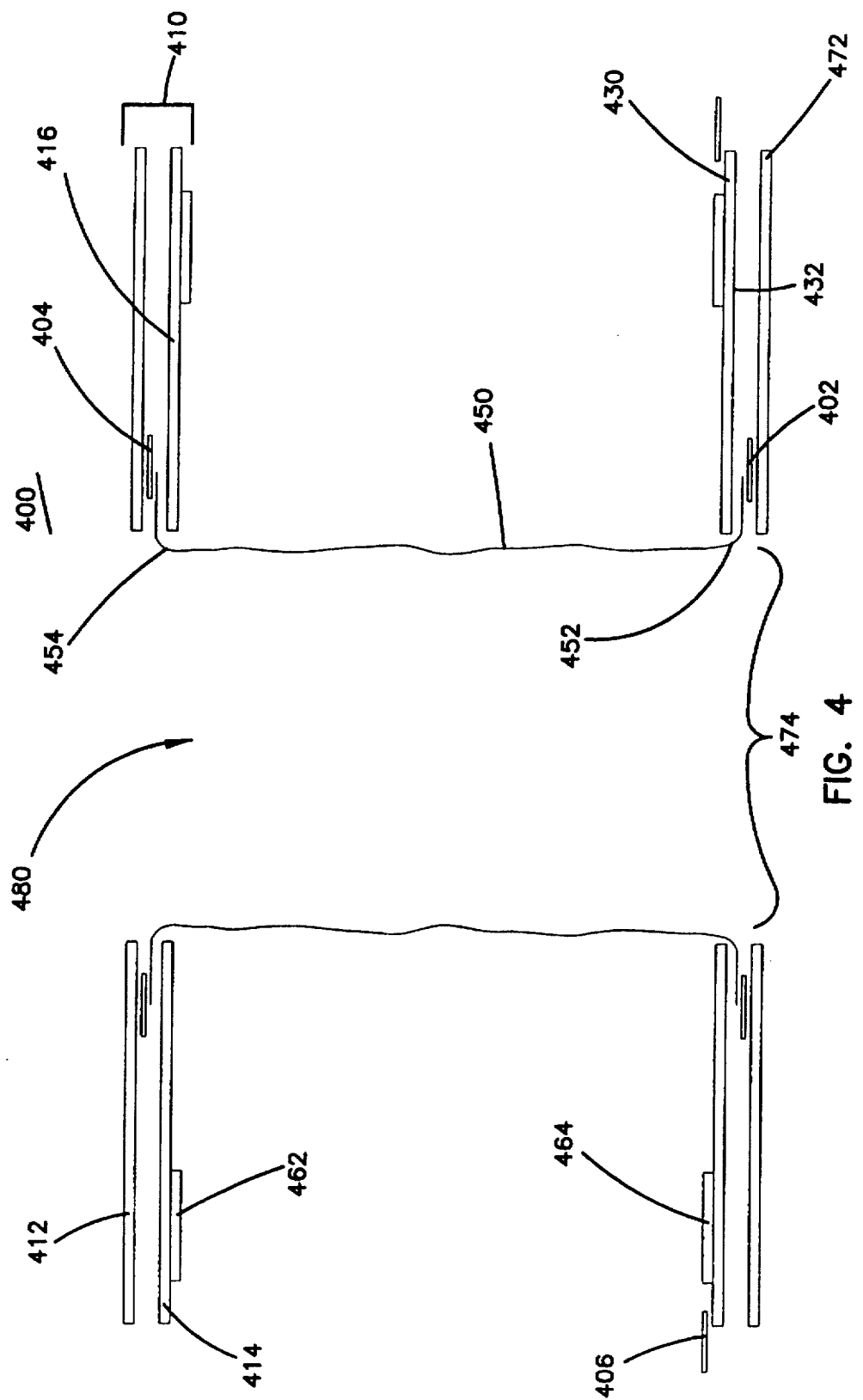
FIG. 4 is a cross sectional view of an exemplary sealing apparatus.

The sealing apparatus 100 may advantageously be attached to the periphery 170 at the end of an assembly process. This, for example, allows the sealing apparatus and periphery to each be independently and completely manufactured prior to attachment together. With reference to FIG. 4, one exemplary process of fabricating a sealing apparatus 400 and attaching the sealing apparatus 400 to a periphery 472 will now be described. The exemplary manufacturing process is provided by way of illustration and not of limitation. One skilled in the art will readily recognize that a number of modifications (such as reordering of steps, use of different materials, and so forth) may be made to the illustrated process. These modifications are intended to be covered by the present invention.

In accordance with the exemplary manufacturing process, the sealing apparatus 400 is formed by attaching one end 452 of a flexible material 450 to a bottom frame 430 and attaching the other end 454 of the flexible material 450 to an upper frame 410 such that the tubular material 450 forms an iris aperture 480 between openings in the two frames 410 and 430. The bottom frame 430 may be attached to the periphery 472 of an environment so that the sealing apparatus 400 may be used to seal an opening 474 in the periphery of the environment. These attachments may form a fluid-resistant seal.

In greater detail, the flexible material end 452 is attached to a bottom surface 432 of the bottom frame 430 using, for example, tape 402. The other flexible material end 454 is attached between two frame members 412 and 414 which form the frame 410. The ends 452 and 454 of the tubular material 450 may be flared to facilitate attachment of the ends 452 to the frames 410 and 430. The end 454 may, for example, be attached to an upper surface 416 of the frame member 414 using a tape 404. The tape 404 may be a double-sided adhesive tape to both attach the flexible material end 454 to the frame 410 as well as to attach the two frame members 412 and 414 together to form the frame 410. Fastening structure 462 and 464, such as hook and loop material, for securing frames 410 and 430 together may be provided on opposing surfaces of the two frames 410 and 430. The sealing apparatus 400 may then be attached to the environment periphery 472 using, for example, a tape 406.

Suitable tapes 402 and 406 for attaching the flexible material 450 to the bottom frame 430 and attaching the sealing apparatus 400 to the environment periphery 472 include adhesive tapes which form fluid-resistant seals, such as the tapes described above, for example. Suitable tape 404 for attaching the flexible material 452 to frame 410 and for attaching frame members 412 and 414 together may include, for example, a double-sided adhesive tape which forms a fluid-resistant seal, such as a 3M Medical double coated tape. The use of tape allows for quick assembly. The use of fluid-resistant tapes disposed about a perimeter of the structure being taped provides a fluid-tight sealing of the environment. However, it should be appreciated, other types of glues, adhesives or fastening means may be used to attach the various structures together. For example, one or more of the frames may be heat-sealed to the flexible material. Likewise, the bottom frame may be heat-sealed to the environment periphery.

Figure 5:
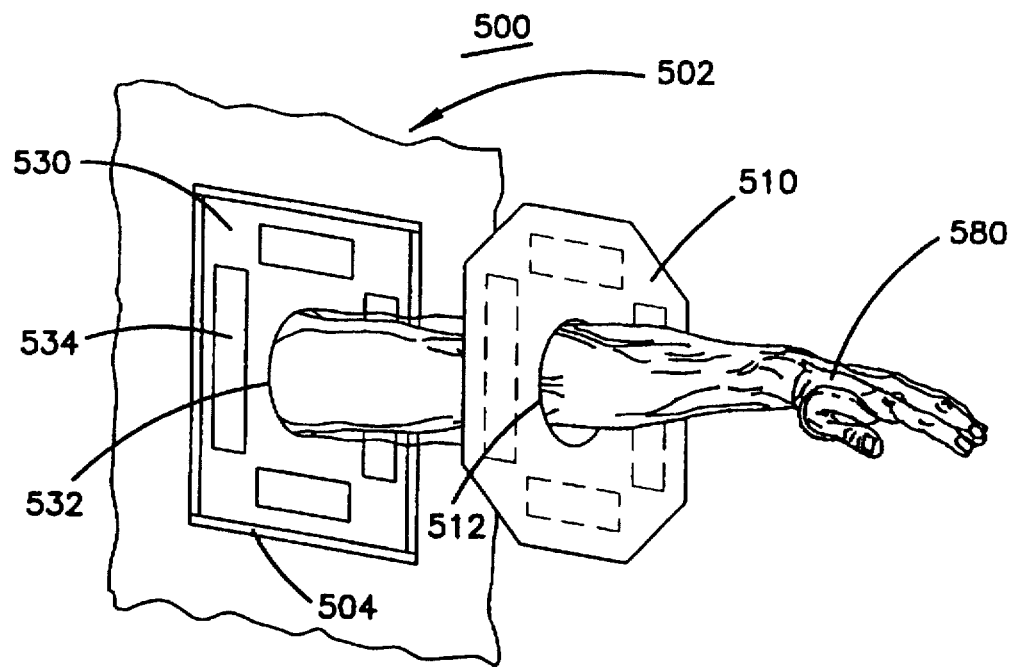
FIG. 5 is an exemplary surgical drape having a sealing apparatus in accordance with one embodiment of the invention.
Figure 6:
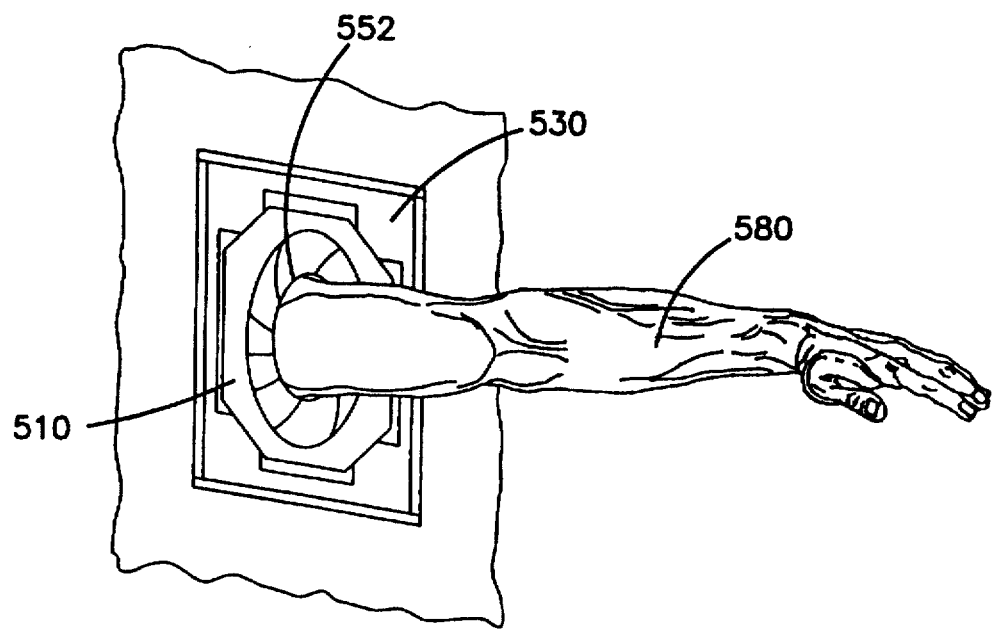
FIG. 6 is another view of the exemplary surgical drape of FIG. 5.

As noted above, the present invention may be used in a wide variety of applications. FIGS. 5 and 6 illustrate one particular use of a sealing apparatus 502 with a surgical drape 500. The sealing apparatus 502 may be similar to sealing apparatus 100 with the openings 512 and 532 of the frames 510 and 530 being sized to receive a limb 580 of a surgical patient. In the illustrated embodiment, the frame 530 is generally attached to the surgical drape 500 using, for example, a tape 504. Preferably, the sealing apparatus is sealingly attached to the drape to form a fluid-resistant seal. Suitable tape 504 includes adhesive tapes, such those discussed above, for example.

The exemplary frame 530 includes fastening structure 534, such as a hook or loop material, for attaching to fastening structure, such as hook or loop material, on the frame 510. It should be appreciated that in other embodiments, different fastening structure may be employed and may be provided on only one or both of the frames, as discussed above. As illustrated in FIG. 6, the frame 510 may be rotated with respect to frame 530 in order to seal the iris aperture 552 about the limb 580 of the patient. The frame 510 may then be pressed against frame 530 to engage the hook and loop fastening system and fix the size of the sealed aperture 552.

Figure 7:
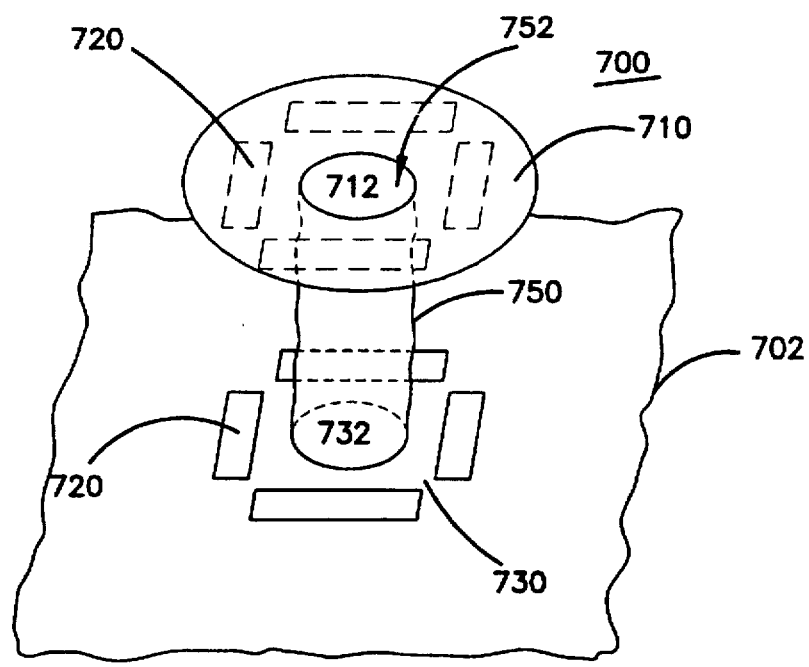
FIG. 7 illustrates another exemplary sealing apparatus in accordance with yet another embodiment of the present invention.
Figure 8:
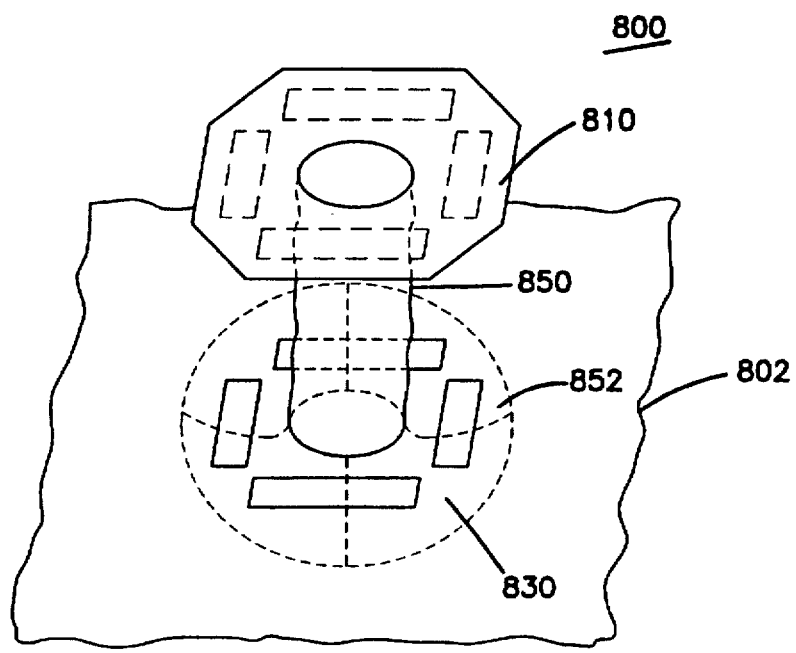
FIG. 8 illustrates still another sealing apparatus in accordance with yet another embodiment of the present invention.

FIGS. 7 and 8 illustrate alternate embodiments of the present invention in which one of the frames of the sealing apparatus is integrally formed with a periphery of an environment. FIG. 7 illustrates a sealing apparatus 700 for sealing an environment defined by a periphery 702. The sealing apparatus 700 generally includes a first frame 710 and a second frame 730 integrally formed from a portion of the periphery 702. The two frames 710 and 730 include openings 712 and 732 and are interconnected by a flexible material 750 which forms an iris aperture 752 between the openings 712 and 732.

In this particular embodiment, the flexible material 750 is integrally formed from the periphery 702 of the environment and is attached to frame 710, for example, in a similar manner as discussed above. One or both of the frames 710 and 730 may include fastening structure 720, for example a hook or loop material, for securing the two frames together and fixing the size of the iris aperture. Where the periphery is relatively flexible (such as with a typical surgical drape), the frame 710 may be relatively flexible or include a relatively flexible portion to more readily conform to the periphery and facilitate securing of the frames together.

FIG. 8 illustrates a sealing apparatus 800 for sealing an environment defined by a periphery 802 such as a surgical drape. The sealing apparatus 800 generally includes a first frame 810 and a second frame 830, integrally formed from a portion of the periphery 802. This embodiment is similar to the sealing apparatus 700 with the exception that the flexible material 850, interconnecting the frames 810 and 830, is not integrally formed with the periphery 802. Rather, one end 852 (shown in dashed lines)of the tubular material 850 is flared and extends along the back side of the periphery 802. The flared end 852 of the flexible material 850 may be attached to the periphery 802 using, for example, a tape. Suitable tapes include adhesive tapes which form fluid-resistant seals, such as those discussed above, for example.

In other embodiments, a flared end of flexible material may extend between two layers of a periphery or along the outer side of a periphery (i.e., the side opposite the sealed environment).

As noted above, the present invention is applicable to sealing apparatus in general. Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications, process and structures.

What is claimed is:

1. A surgical drape, comprising:
    a drape sheet having a first frame defining an opening capable of receiving an appendage;
    a second frame defining an opening capable of receiving the appendage; and
    a flexible material rotatably interconnected between the first frame and second frame, the flexible material forming an iris aperture capable of receiving the appendage;
    wherein the size of the iris aperture can be adjusted by rotating the second frame with respect to the first frame.

2. The surgical drape of claim 1, wherein at least one of the first frame and second frame includes fastening structure for securing the first frame with respect to the second frame and fixing the size of the iris aperture.

3. The surgical drape of claim 2, wherein one of the first frame and second frame includes a loop material and the other one of the first frame and the second frame includes a hook material, wherein the hook material and loop material may be interconnected to secure the first frame with respect to the second frame.

4. The surgical drape of claim 3, wherein the hook material and the loop material have a slim profile.

5. The surgical drape of claim 1, wherein the first frame is integrally formed from a portion of the drape sheet.

6. The surgical drape of claim 1, wherein the first frame is attached to the drape sheet.

7. The surgical drape of claim 6, wherein the drape sheet defines an opening, the first frame opening overlapping with the drape sheet opening.

8. The surgical drape of claim 1, wherein the flexible material is formed from a plastic material.

9. An apparatus for sealing an environment defined by a periphery, comprising:
    a first frame comprising an opening in a sheet material and being disposed on the periphery of the environment;
    a second frame comprising an opening in a sheet material; and
    a flexible material rotatably interconnected between the first frame and second frame, the flexible material forming an iris aperture;
    wherein the size of the iris aperture may be adjusted by rotating the second frame with respect to the first frame.

10. The apparatus of claim 9, wherein the first frame may be secured with respect to the second frame to fix the size of the iris aperture.

11. The apparatus of claim 10, wherein one of the first frame and second frame includes a loop material and the other one of the first frame and the second frame includes a hook material, wherein the hook material and loop material may be interconnected to secure the first frame with respect to the second frame.

12. The apparatus of claim 9, wherein the flexible material is sealingly attached to the first frame and the second frame using tape.

13. The apparatus of claim 9, wherein the iris aperture may be closed by rotating the second frame with respect to the first frame.

14. The apparatus of claim 9, wherein the first and second frame openings are capable of receiving a limb, and wherein the size of the iris aperture may be adjusted to form a seal about the limb.

15. The apparatus of claim 9, wherein the first frame is integrally formed from a portion of the periphery.

16. The apparatus of claim 9, wherein the first frame is attached to the periphery.

17. A method of forming a sealing aperture for a surgical drape, comprising:

providing a first frame with an opening and a second frame with an opening;

attaching a first end of a tubular material to the first frame and a second end of the tubular material to the second frame such that the tubular material forms an iris aperture between the first frame opening and the second frame opening; and attaching the first frame to the surgical drape.

18. The method of claim 17, wherein attaching the first end of the tubular material to the first frame includes:

disposing the first end of the tubular material through the opening of the first frame;

positioning the first end of the tubular material against a side of the first frame opposite the second frame; and taping the first end of the tubular material to the side of the first frame.

19. The method of claim 17, wherein attaching the second end of the tubular material to the second frame includes:

disposing the second end of the tubular material through the opening of the second frame;

positioning the second end of the tubular material against a side of the second frame opposite the second frame; and taping the second end of the tubular material to the side of the second frame.

20. The method of claim 17, wherein attaching the first frame to the surgical drape includes taping the first frame to the surgical drape.

* * * * *

UNITED STATES PATENT AND TRADEMARK OFFICE
CERTIFICATE OF CORRRECTION

PATENT NO. : 5,832,925
DATED : November 10, 1998
INVENTOR(S) : Robert J. Rothrum It is certified that error appears in the above-identified patent and that said Letters Patent is hereby corrected as shown below:

Title page, item [56], insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 2 | 6 | 9 | 5 | 6 | 08 | 11/30/54 | Gibbon | 128 | 30 | |
| | | | | | | | | | | | | |

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | WO | 95/ | 2 | 7 | 4 | 6 | 8 | 19.10.95 | | | | | |
| | WO | 97/ | 1 | 1 | 6 | 4 | 2 | 03.04.97 | | | | | |
| | DE | 8 | 7 | 0 | 7 | 8 | 17 | 10.09.87 | Germany | | | | x |
| | | | | | | | | | | | | | |

OTHER DOCUMENTS (Including Authors, Title, Date, Pertinent Papers, etc.)

PCT International Search Report for PCT/US98/07478

Signed and Sealed this

Thirtieth Day of November, 1999

*Attest:*

Q. TODD DICKINSON

*Attesting Officer*    *Acting Commissioner of Patents and Trademarks*